United States Patent
Ninomiya et al.

[11] Patent Number: 5,932,235
[45] Date of Patent: Aug. 3, 1999

[54] JELLIED MEDICINAL COMPOSITION FOR ORAL ADMINISTRATION

[75] Inventors: Hiroshi Ninomiya, Omiya; Toshio Shimizu, Tokyo; Masatake Dairaku, Omiya; Takeshi Komagata, Tokyo; Masayo Misawa, Omiya, all of Japan

[73] Assignee: OHTA Pharmaceutical Co., Ltd., Saitama, Japan

[21] Appl. No.: 09/091,977

[22] PCT Filed: Jul. 17, 1996

[86] PCT No.: PCT/JP96/01993

§ 371 Date: Jun. 23, 1998

§ 102(e) Date: Jun. 23, 1998

[87] PCT Pub. No.: WO97/25024

PCT Pub. Date: Jul. 17, 1997

[30] Foreign Application Priority Data

Jan. 12, 1996 [JP] Japan .......................................... 8-4288
Jan. 12, 1996 [JP] Japan .......................................... 8-4289

[51] Int. Cl.$^6$ .............................. A61K 6/00; A61K 7/00; A61K 9/20; A61K 9/48

[52] U.S. Cl. .......................... 424/401; 424/451; 424/464

[58] Field of Search ...................................... 424/401, 451, 424/464

[56] References Cited

U.S. PATENT DOCUMENTS 5,648,093  7/1997  Gole et al. ............................... 424/484

Primary Examiner—Thurman K. Page
Assistant Examiner—Sharon Howard
Attorney, Agent, or Firm—Jones & Askew

[57] ABSTRACT

A medical composition for oral administration is formulated into a jellied form preferably using a base containing carrageenan, locust bean gum, and polyacrylic acid or a partly neutralized product or salt thereof. The jellied medical composition for oral administration is contained in a disposable container made of a synthetic resin and composed of a shell being deformable under forcing and capable of containing the composition therein, a ring neck with a small diameter connected to the shell, and a handle serving as the closed end of the neck and connected to the neck in a breakable manner, wherein the neck is opened to provide a spout for pouring the composition when the handle is broken away from the neck.

9 Claims, 4 Drawing Sheets

JELLIED MEDICINAL COMPOSITION FOR ORAL ADMINISTRATION

TECHNICAL FIELD

The present invention relates to a jellied medical composition for oral administration, specifically to a jellied medical composition for oral administration which is easily taken by patients of advanced age or patients with dysphagia, more specifically to a jellied medical composition for oral administration which does not easily cause syneresis and retains preservation stability at the medical level in terms of maintenance of appearance and pH of the composition and maintenance of dispersibility and the contents of the effective components in the composition, and further to a jellied medical composition for oral administration packed in a disposable container a predetermined dose of which can be taken with solidity appropriate for swallowing and with good texture, which is suitable for improvement of compliance.

BACKGROUND ART

In future medicine, it is indispensable to solve medical problems in the aged society. One of the problems of such medicine for the aged is great difficulty for patients with advanced age in taking any of the currently used dosage forms of medical compositions for oral administration. Patients with dysphagia have also been suffering from this problem that it is difficult to take a medical composition for oral administration.

For example, the medical compositions for oral administration listed in the general medical preparations of Japanese Pharmacopoeia include tablets, capsules, pills, powders, liquid, syrup, and the like. Such dosage forms are not easily taken by patients of advanced age, particularly patients with dysphagia. Among these, liquid and syrup preparations are easily taken by them as compared with the other dosage forms. However, because of liquid, there are problems to be overcome, when formulating into dosage forms, such as masking of bitterness of effective components, their dispersibility and stability. Particularly, patients with dysphagia cannot take such a medical composition because they are choked by water. Ito et al. (Monthly Pharmaceutical, Vol. 37, No. 11, p 45–49 (1995)) reported that patients with advanced age cannot easily take tablets or capsules depending on their sizes. Thus, it has been desired to develop new pharmaceutical preparations that are easily taken by patients of advanced age or patients with dysphagia.

In order to solve the above problems for patients of advanced age, Ito et al. proposed to use liquid preparations having high viscosity as one of the medical preparations for them (Monthly Pharmaceutical, Vol. 37, No. 11, p 45–49 (1995)). Another report (Clinical Nutrition, Vol. 79, No. 1, p 22–39 (1991)) describes that liquid preparations having high viscosity are favorably used as one of the dosage forms of medical preparations that can be easily taken by patients with dysphagia. Thus, from general viewpoints, it has been considered that liquid preparations having high viscosity are appropriate as a dosage form of medical preparations for oral administration that can be easily taken by patients of advanced age and patients with dysphagia.

Actually for clinical use for, it was reported that, as nosocomial medicines, a highly viscous liquid pharmaceutical preparation was prepared usually using one or two or more of gelatin, pectin, xanthan gum, carrageenan, and the like upon use or with the short applicable term to administer it to patients who could not easily take usually used medical preparations for oral administration (Medical Care and New Drugs, Vol. 13, No. 11, p 208–214 (1994), Pharmacy, Vol. 42, No. 11, p 53–59 (1991)). However, even the above-described highly viscous liquid pharmaceutical preparations are still unsatisfactory in easiness to take. Further, these preparations are used only for a limited period of short time since it is difficult to secure their long-term stability. In other words, there are such problems that the viscous pharmaceutical preparations cannot keep viscosity to become an aqueous state, that their original appearances are difficult to maintain, and that their preservation stability including maintenance of the contents of the effective components is not sufficient. Accordingly, it has been desired to develop a medical composition for oral administration free from the above problems including insufficiency in easiness to take the highly viscous liquid preparations and poor preservation stability of them.

On the other hand, it is not known so far that a medical preparation for oral administration is used in a jellied dosage form. Edible jellied compositions include sweet jellies used in food industry, which are prepared usually using as a base one or two or more of gelatin, pectin, xanthan gum, carrageenan, locust bean gum, mannnan, and the like. Their appearances are secured usually for about one year under preservation at room temperature or in a cool place. However, none of them can keep preservation stability in terms of pH and the contents of the effective components in addition to appearance at the medical level tests (for example, the preservation test at room temperature for three years, or an acceleration test at 40° C. and 75% RH for six months).

As described above, there has been no case of using pharmaceutical preparations for oral administration in a jellied form as a dosage form that can be easily taken by patients of advanced age or patients with dysphagia. Further, at present, no base used for such a jellied pharmaceutical preparation for oral administration is available, which shows preservation stability in terms of maintenance of appearance and pH of the formulated jellied composition and maintenance of dispersibility and the contents of the effective components in the composition, stability of which is bearable to the medical level tests, such as a preservation test at room temperature for three years, or an acceleration test at 40° C. and 75% RH for six months. In addition, there is no information about a disposable container having a shape that makes it possible to take such a jellied medical composition for oral administration with solidity appropriate for swallowing and with good texture, and to improve compliance.

DISCLOSURE OF THE INVENTION

The present invention was made to solve the above problems and an object of the present invention is to provide a jellied medical composition for oral administration, which is easily taken by patients of advanced age or patients with dysphagia, specifically a jellied medical composition for oral administration which does not easily cause syneresis and retains preservation stability at the medical level in terms of maintenance of appearance and pH of the composition and maintenance of dispersibility and the contents of the effective components in the composition, and further a jellied medical composition for oral administration packed in a disposable container, whose predetermined dose can be taken with solidity appropriate for swallowing and with good texture, which is suitable for improvement of compliance.

As a result of intensive investigation to achieve the above object, the present inventors confirmed that the medical composition for oral administration can be easily taken by patients of advanced age or patients with dysphagia by making it a jellied form. Further, it was found that preservation stability can be secured at the medical level in terms of maintenance of appearance and pH of the composition and maintenance of dispersibility and the contents of the effective components in the composition, by preparing the above-described jellied medical composition for oral administration together with carrageenan and locust bean gum as a base, preferably with polyacrylic acid or a partly neutralized products or salts thereof in addition to the above components so that syneresis hardly occurs. Furthermore, it was found that the jellied medical composition for oral administration can be taken at a predetermined dose with solidity appropriate for swallowing and with good texture and can improve compliance, by packing the jellied medical composition for oral administration in a disposable container having a specific shape. Thus, the present invention was completed.

Namely, the present invention provides a jellied medical composition for oral administration.

The jelly base of the jellied medical composition for oral administration of the present invention is preferably a base containing carrageenan and locust bean gum. In the case of using a base containing carrageenan and locust bean gum as a jelly base for the composition of the present invention, the contents of carrageenan and locust bean gum are preferably 0.01 to 1.0 wt % and 0.01 to 1.0 wt %, respectively, based on the total weight of the composition.

The jellied medical composition for oral administration of the present invention more preferably contain polyacrylic acid or its partly neutralized products or salts thereof, preferably sodium polyacrylate, in addition to carrageenan and locust bean gum as described above used as a base. In this case, the content of polyacrylic acid or its partly neutralized products or salts preferably ranges from 0.005 to 0.05 wt % based on the total weight of the composition.

The present invention also provides a jellied medical composition packed in a disposable container which is made of a synthetic resin and composed of a shell being deformable under forcing and capable of containing the jellied medical composition for oral administration therein, a ring neck with a small diameter connected to the shell, and a handle serving as the closed end of the neck and connected to the neck in a breakable manner, wherein the neck is opened to provide a spout for pouring the jellied medical composition for oral administration when the handle is broken away from the neck.

With respect to the above jellied medical composition for oral administration packed in the disposable container of the present invention, it is preferable to make the content of the jellied medical composition for oral administration in the disposable container equal to a dose of the composition and to make the diameter of the spout formed when the handle of the disposable container is broken away from the neck 1 to 15 mm.

The present invention will be described in detail below.
(1) The jellied medical composition for oral administration of the present invention The jellied medical composition for oral administration of the present invention is characterized by being a jellied form. Any medical composition for oral administration formulated into a jellied form is included in the jellied medical composition for oral administration of the present invention without particularly being limited. The jellied composition usually has such a structure that a dispersion medium of the base is retained in the pit of the skeleton of the solid phase composed of the base. In the jellied medical composition for oral administration of the present invention, a pharmaceutically effective ingredient is contained in the solved, dispersed, suspended, or the like state in the above-described dispersion medium.

Any base usually used for jellied compositions for food can be used as the base to be used in the jellied medical composition for oral administration of the present invention without particularly being limited. Such a base may be one or two or more selected from, for example, gelatin, pectin, xanthan gum, carrageenan, locust bean gum, mannan, or the like. Among these, it is preferable to use a base containing carrageenan and locust bean gum in the jellied medical composition for oral administration of the present invention in view of preservation stability.

The above-described carrageenan includes κ, ι, and λ type. Though any of these types of carrageenan can be used in the jellied medical composition for oral administration of the present invention, κ-carrageenan is preferably used. The content of carrageenan in the jellied medical composition for oral administration of the present invention ranges preferably from 0.01 to 1.0 wt %, more preferably from 0.05 to 0.7 wt %, most preferably from 0.08 to 0.5 wt %, based on the total weight of the medical composition.

Locust bean gum usually used as a base in jellied compositions is used in the jellied medical composition for oral administration of the present invention without particularly being limited. The content of locust bean gum in the jellied medical composition for oral administration of the present invention ranges preferably from 0.01 to 1.0 wt %, more preferably from 0.05 to 0.7 wt %, most preferably from 0.08 to 0.5 wt %, based on the total weight of the medical composition.

In the jellied medical composition for oral administration of the present invention, it is preferable to use a base containing carrageenan and locust bean gum as described above for retaining preservation stability. More preferably, the base further contains polyacrylic acid or a partly neutralized product or salt thereof (hereinafter generically referred to as "polyacrylic acid compound") in view of preservation stability. In the case of adding a polyacrylic acid compound to the jellied medical composition for oral administration of the present invention, one kind thereof can be added alone, or two or more thereof can be added in combination. The polyacrylic acid compound preferably used in the base of the jellied medical composition for oral administration of the present invention is sodium polyacrylate, which is one of salts of polyacrylic acid.

The polyacrylic acid compound can be used in the jellied medical composition for oral administration of the present invention in any amount as long as the amount is generally fallen within the range accepted as an additive for use in medical compositions. Specifically, the content of the polyacrylic acid compound ranges preferably from 0.005 to 0.05 wt %, more preferably from 0.008 to 0.04 wt %, most preferably from 0.01 to 0.02 wt %, based on the total weight of the medical composition.

Further, in addition to the above three components, the base of the jellied medical composition for oral administration of the present invention may contain the compounds conventionally known to be used as a base in jellied compounds.

As the dispersion medium for the base, which is contained in the jellied medical composition for oral administration of the present invention so that the dispersion medium of the base is retained in the pit of the skeleton of the solid phase composed of the base, any liquid can be used as long as it is generally acceptable as additives for medicines, it can be orally administered, and the base can be dispersed therein at an appropriate temperature. In the dispersion medium retained in the pit of the skeleton of the solid phase composed of the base, various arbitrary components can be contained in the solved, dispersed, suspended, or the like state as well as the above-described medically effective components. Specifically, the dispersion medium used in the jellied medical composition for oral administration of the present invention is exemplified by water or a mixed solution of water and polyhydric alcohol. Examples of polyhydric alcohol include glycerol, propylene glycol, and the like.

As the medically effective components contained in the jellied medical composition for oral administration of the present invention, any medically effective components can be used, without particularly being limited, as long as they are used as the medically effective components in the usual medical compositions for oral administration. The medically effective components may be contained in the jellied medical composition for oral administration in such an amount that each effective component can be taken at an appropriate dose when patients take a predetermined amount of the composition. In addition to the above components, the jellied medical composition for oral administration of the present invention may further contain various arbitrary components that are acceptable as the additives for medicines and can be orally administered, including a stabilizer, a buffering agent, a sweetener, an emulsifier, a dispersant, a preservative, an aromatic, and the like, if required.

Examples of the stabilizer include ascorbic acid, sodium edetate, tocopherol, and the like. Examples of the buffering agent include potassium chloride, sodium chloride, citric acid, sodium citrate, dipotassium phosphate, sodium phosphate, and the like. Examples of the sweetener include sodium saccharin, purified sugar, D-sorbitol, D-mannitol, and the like. Examples of the emulsifier include polyoxyethylenesorbitan monooleate, sodium lauryl sulfate, and the like. Examples of the dispersant include water-soluble polymers such as carboxymethylcellulose, sodium alginate, hydroxypropylcellulose, hydroxyethylcellulose, and the like. Examples of the preservative include ethyl paraoxybenzoate (ethyl paraben), methyl paraoxybenzoate (methyl paraben), and the like. Examples of the aromatic include flavors, essential oil, and the like such as menthols or fruit juice.

The jellied medical composition for oral administration of the present invention can be prepared by the same method as the preparation method for the conventionally used jellied composition except for adding the above-described components. Specifically, the base for the jellied composition is dispersed in the dispersion medium at an appropriate temperature, the medically effective components are dissolved, dispersed, or suspended therein with regulating the temperature, and, thereafter, the mixture is cooled to cause gelation. In the preparation of the composition of the present invention, the above arbitrary components can be added at any time before gelation of the jellied medical composition for oral administration of the present invention, for example, at the time of dispersing the base in the dispersion medium or at the time of adding the medically effective components in the dispersion thus prepared.

Further, the method of preparing the jellied medical composition for oral administration of the present invention is specifically exemplified as follows. First, an appropriate amount of warm water having a temperature of from 80 to 90° C. is added as the dispersion medium to the above base and the arbitrary components to disperse, dissolve, or suspend them by stirring with a stirrer or a vacuum stirrer. Alternatively, an appropriate amount of water is added at a room temperature as the dispersion medium to the base and the arbitrary components which are dispersed, dissolved, or suspended therein by heating the resulting mixture to 80 to 90° C. under stirring with a stirrer or the like. The stirrer and the vacuum stirrer to be used are preferably models bearable to heat. Then, the thus-obtained dispersion, solution, or suspension is cooled to 65 to 55° C. and the medically effective components are added thereto followed by stirring. This is allowed to stand at ordinary temperature for 1 to 2 hours, or at 10° C. or lower for about 1 hour, though it depends on the volume, to make the liquid gelled to give the jellied medical composition for oral administration of the present invention.

Upon the gelation in the preparation of the above-described jellied medical composition for oral administration of the present invention, the composition is divided into a dose in advance to thereby improve convenience of administration. Further, the medical preparation having a dosage form further excellent in easiness to be taken and use can be obtained by incorporating a dose of the composition in the disposable container as described below.

According to the present invention, medical compositions for oral administration are made to be easily taken by patients of advanced age and patients with dysphagia by making them into a jellied form. When the medically effective components contained in the jellied medical composition for oral administration of the present invention have taste that is not to be easily taken like bitterness, the present invention is remarkably excellent in an effect to mask the taste to make it to be easily taken. Since the medical composition for oral administration of the present invention is in the jellied form, the medically effective components neither aggregate nor precipitate if they are insoluble in the dispersion medium of the base. Thus, this is the medical composition for oral administration remarkably excellent in dispersibility.

Further, the jellied medical composition for oral administration of the present invention comprising a base having such a specific composition as containing carrageenan and locust bean gum, preferably polyacrylic acid or a partly neutralized product or salt thereof in addition to the above components is a jellied medical composition for oral administration having secured preservation stability at the medical level in terms of maintenance of appearance and pH of the composition and maintenance of dispersibility and the contents of the active ingredients in the composition. This jellied medical composition for oral administration of the present invention enables administration of the jellied medical composition for oral administration to patients of advanced age and patients with dysphagia without preparing upon use in the hospital and administering within the short period of the application and thus enables domestic use within generally long-term period.

Among the jelly base used in the above-described jellied medical composition for oral administration of the present invention, the jelly base containing carrageenan, locust bean gum, and polyacrylic acid or a partly neutralized product or salt thereof has the novel composition. The jellied composition obtained by using this jelly base does not easily cause syneresis and is excellent in preservation stability as compared with the conventionally known jellied compositions. Such a jelly composition can be applied to the jellied compositions other than the jellied medical composition for oral administration of the present invention, such as food, cosmetics, agricultural chemicals, miscellaneous goods, with being suitably applied to food.

(2) The jellied medical composition for oral administration packed in a disposable container according to the present invention The jellied medical composition for oral administration packed in a disposable container according to the present invention is provided to improve easiness to take and safety of the above-described jellied medical composition for oral administration. This has such configuration as the above-described jellied medical composition for oral administration in the container which is made of synthetic resin and composed of a shell being deformable under forcing and capable of containing the jellied medical composition for oral administration therein, a ring neck with a small diameter connected to the shell, and a handle serving as the closed end of the neck and connected to the neck in a breakable manner, wherein the neck is opened to provide a spout for pouring the jellied medical composition when the handle is broken away from the neck.

In the jellied medical composition for oral administration packed in a disposable container according to the present invention, the content of the jellied medical composition for oral administration in the disposable container is preferably 1 to 25 ml taking the dose, the size and portability of the container, into consideration. When the same amount as the dose is contained, persons, who need to take it, can take a correct dose without taking an incorrect dose.

In the jellied medical composition for oral administration packed in a disposable container according to the present invention, the diameter of the spout formed, when the handle of the disposable container is broken away from the neck, is not particularly limited as long as it has such a size that the jellied medical composition for oral administration is pushed out of the spout of the container to give the size easily to be taken, for example, swallowed without mastication. Specifically, it preferably ranges from about 1 to 15 mm. The diameter of the spout is determined depending on the strength of the jellied medical composition for oral administration and symptoms of the patients.

According to the jellied medical composition for oral administration packed in a disposable container of the present invention, any jellied medical composition for oral administration as described above can be used as the jellied medical composition for oral administration packed in the container without particularly being limited. It is preferable to use the jellied medical composition for oral administration having a specific base composition of the present invention, that is, the base containing carrageenan and locust bean gum, preferably in addition to these components, polyacrylic acid or a partly neutralized product or salt thereof, in view of preservation stability.

In the disposable container used in the present invention, the shell is deformable under forcing so as to push out the jellied medical composition for oral administration. Accordingly, the strength of the jellied medical composition for oral administration packed in the container is preferably about 30 to 800 g so that the patients are not burdened with the power necessary for pushing.

In this connection, the jelly strength is defined as follows. A jelly is prepared in a 200-ml beaker. The beaker is placed on the measuring table of rheometer CR-200D (manufactured by Kabushiki Kaisha San Kagaku). When the pressure-sensitive bar for the jelly strength test is inserted into the jelly at the position of 20 mm from the surface, the maximum load is measured to serve as the jelly strength.

In the disposable container used in the present invention, the handle may be broken away from the neck by means of scissors. If the handle is made breakable by twisting or folding it against the shell, it is convenient, particularly when taking the composition at a visiting place.

A set of the disposable containers used in the present invention can be prepared by serially connecting a number of container and making them separable from each other. In such a form, it is convenient to care and carry the jellied medical composition for oral administration.

The jellied medical composition for oral administration packed in the disposable container of the present invention can be obtained by incorporating the jellied medical composition for oral administration in the disposable container. According to the present invention, the jellied medical composition for oral administration prepared by the above-described method is packed, prior to its gelation, in the disposable container in a predetermined amount in accordance with the usual method and sealed to give the jellied medical composition for oral administration packed in the disposable container having the above-described shape. Thereafter, the jellied medical composition for oral administration gels in the container. When taking it, the resulting gel is crushed into an appropriate size to be taken when it is pushed out of the spout of the container.

As described above, since the jellied medical composition for oral administration packed in the disposable container of the present invention is crushed into an appropriate size to be taken when it is squeezed out of the spout of the container, it can be easily swallowed without mastication. When a bedridden patient with dysphagia takes the jellied medical composition for oral administration, there is no risk that the patient chokes over the composition. Thus, the jellied medical composition for oral administration packed in the disposable container of the present invention is highly useful in both of easiness to take and safety and greatly contributes to improve compliance.

Next, embodiments of the jellied medical composition for oral administration packed in the disposable container of the present invention will be illustrated based on FIG. 1 through FIG. 8.

FIG. 1 through FIG. 4 each shows an embodiment of the jellied medical composition for oral administration packed in the disposable container (hereinafter maybe referred to as "container") of the present invention; FIG. 1 shows its front view, FIG. 2 shows its side view, FIG. 3 shows its top view, and FIG. 4 is its oblique view showing the configuration at the time of use.

Container 1 is formed in one united body with soft synthetic resin and has shell 2, neck 3, and handle 4. Shell 2 is composed of upper part 2a whose section is in an about elliptical ring form and plain board-like lower part 2b. The section of the tip of upper part 2a gradually becomes smaller upward. The inside of upper part 2a is storage part 2c in which a predetermined amount of the medical composition for oral administration is contained. Upper part 2a is formed to be deformable under forcing by nipping it by fingers.

Neck 3 is connected with the upper end of upper part 2a of shell 2. Neck 3 is in a hollow ring form and its inner space is communicated with storage part 2c.

Handle 4 is connected with the upper end of neck 3. Handle 4 connected with neck 3 has round body part 4a capable of closing the inner space of neck 3 and plain board part 4b rising from the upper surface of round body part 4a. Thick part 4c is formed around plain board part 4b.

Connecting part 5 which connects round body part 4a of handle 4 with neck 3 is made thinner than the other parts. Connecting part 5 is broken when handle 4 is twisted against shell 2 so that the tip of neck 3 is opened to form spout 6.

FIG. 4 shows a configuration that connecting part 5 is broken as described above. In this configuration, when upper part 2a of shell 2 is pressed by nipping it by fingers, the jellied medical composition for oral administration in storage part 2c is pushed out through spout 6.

FIG. 5 through FIG. 7 show another embodiment of the jellied medical composition for oral administration packed in the disposable container used in the present invention; FIG. 5 is its front view, FIG. 6 is its side view, and FIG. 7 is its oblique view showing the configuration at the time of use. In the following, the same numerals are used for the same parts as in the jellied medical composition for oral administration packed in the disposable container as explained for FIG. 1 through FIG. 4 to omit their explanation and only differences from the above jellied medical composition for oral administration packed in the disposable container are demonstrated.

Shell 2 and handle 4 are formed to have the same width over their full length. Board-like part 2d formed at the upper end of upper part 2a of shell 2 is connected with handle 4 to form one united body. Connecting part 7 therebetween is made thinner in a breakable manner.

Neck 3 is made extremely short in the axial direction and formed between shell 2 and handle 4 in a thin constricted form. Neck 3 is connected with cylindrical part 4d formed at handle 4. The inner space of neck 3 is closed by cylindrical part 4d.

In this container 1, neck 3 and connecting part 7 are broken when handle 4 is twisted against shell 2 and the tip of neck 3 is opened to form spout 6. FIG. 7 shows a configuration that neck 3 and connecting part 7 are broken as described above. In this configuration, when upper part 2a of shell 2 is pressed by nipping it by fingers, the jellied medical composition for oral administration in storage part 2c is pushed out through spout 6.

In both containers 1 above, since the jellied medical composition for oral administration is crushed when it passes through spout 6, patients can easily take it without coughing and being choked. Thus, it is very safe. Further, a spoon and the like tools subserving administration are not necessary because the composition can be directly administered to the patient's mouth from spout 6 of container 1. If the content of the jellied medical composition for oral administration in storage part 2c is made the same as the dose, persons, who need to take it, can take its correct dose without taking an incorrect dose. In both containers 1 above, spout 6 can be opened without using scissors or the like. Thus, it is extremely convenient, particularly when taking it at a visiting place.

If a set of containers 1 is formed by serially connecting a number of them and each container 1 is made separable from each other, it is beneficial to care or carry the jellied composition. FIG. 8 is a front view showing an embodiment of the above-described set of containers 1 prepared by serially connecting a number of them. Connecting parts 8 between each container 1 are made thin so as to be easily broken by hand.

BEST MODE FOR CARRYING OUT THE INVENTION

The present invention will be described more specifically with reference to Examples as follows.

EXAMPLES 1 AND 2

Domperidone Jelly

Figure 1:
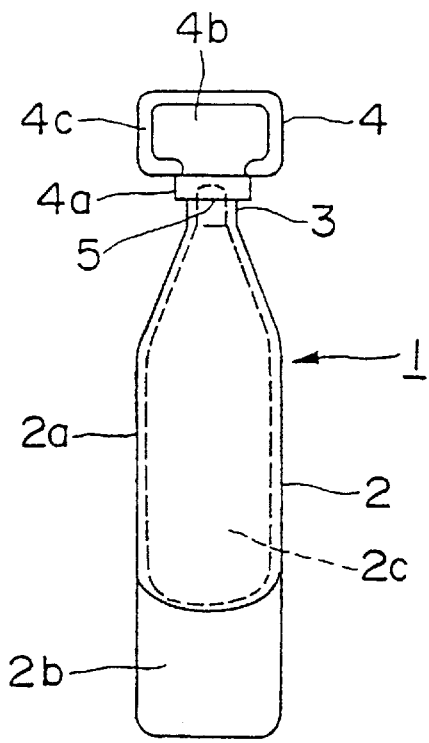
FIG. 1 is a front view of an embodiment of the jellied medical composition for oral administration packed in the disposable container of the present invention.
Figure 2:
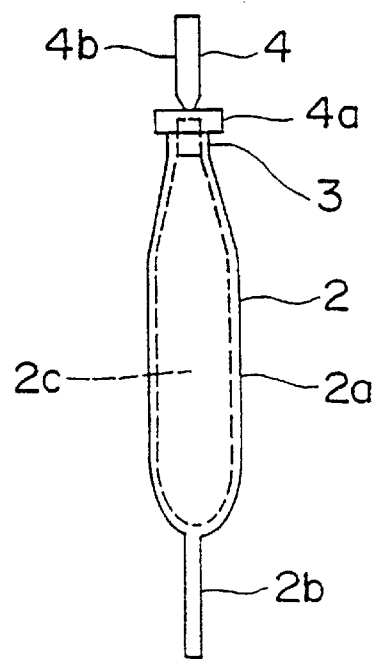
FIG. 2 is a side view of an embodiment of the jellied medical composition for oral administration packed in the disposable container of the present invention.
Figure 3:
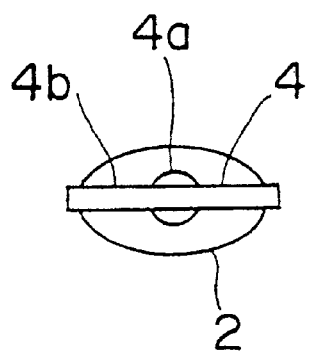
FIG. 3 is a top view of an embodiment of the jellied medical composition for oral administration packed in the disposable container of the present invention.
Figure 4:
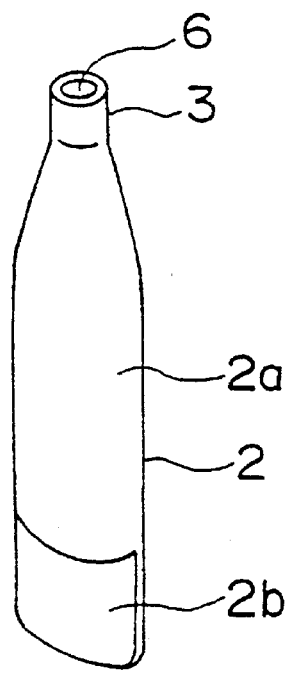
FIG. 4 is an oblique view showing a configuration of an embodiment of the jellied medical composition for oral administration packed in the disposable container of the present invention at the time of use.
Figure 5:
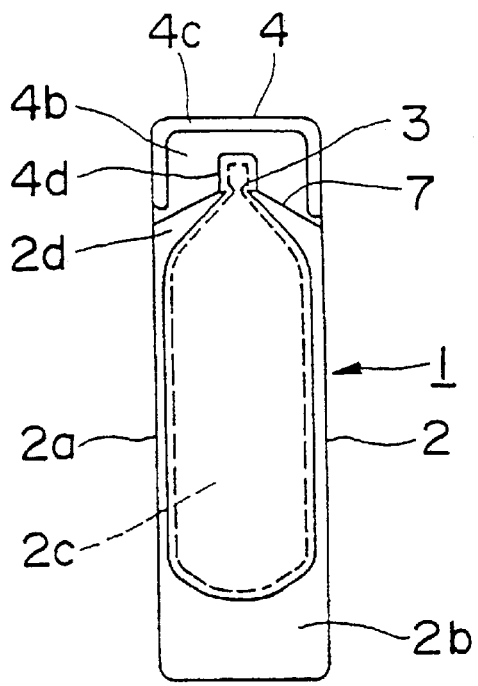
FIG. 5 is a front view of another embodiment of the jellied medical composition for oral administration packed in the disposable container of the present invention.
Figure 6:
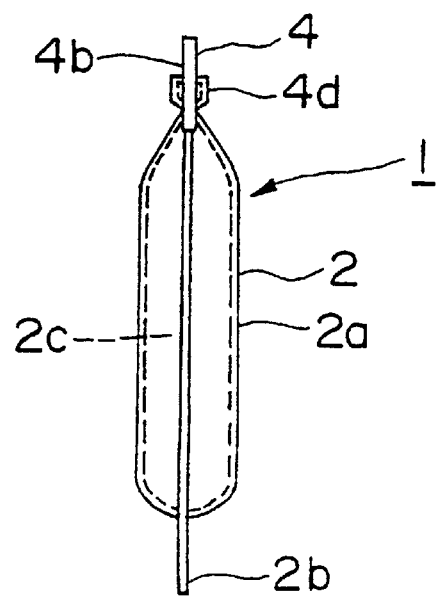
FIG. 6 is a side view of another embodiment of the jellied medical composition for oral administration packed in the disposable container of the present invention.
Figure 7:
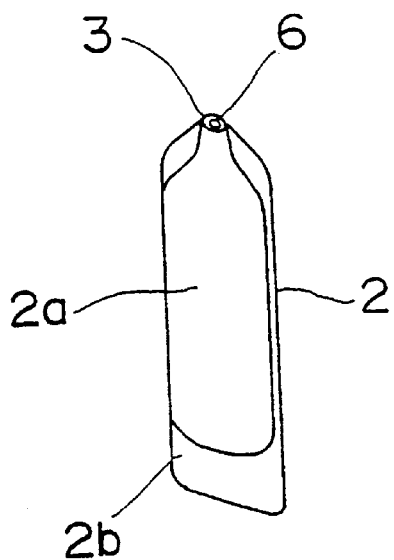
FIG. 7 is an oblique view showing a configuration of another embodiment of the jellied medical composition for oral administration packed in the disposable container of the present invention at the time of use.
Figure 8:
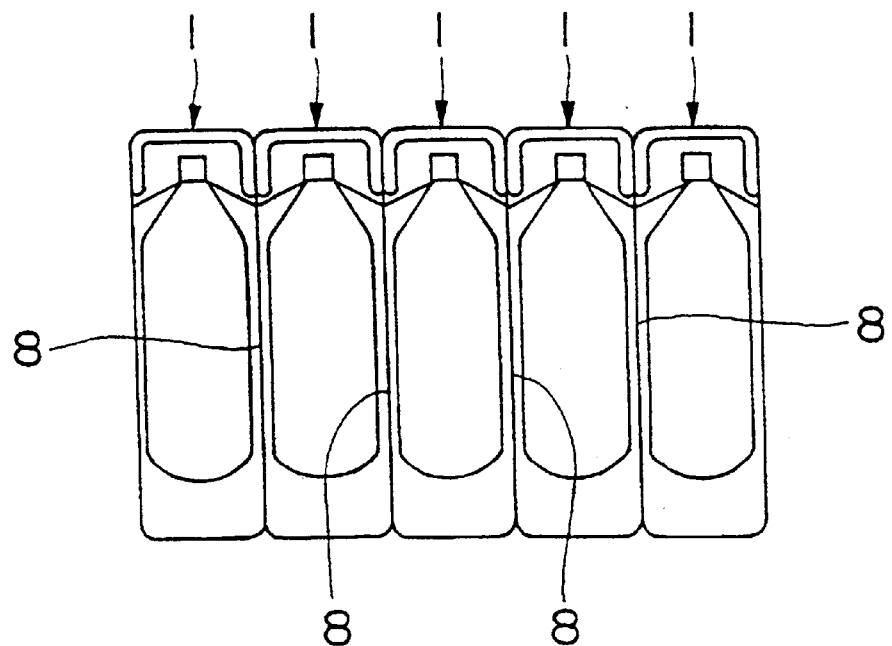
FIG. 8 is a front view showing another embodiment of the jellied medical composition for oral administration packed in the disposable container of the present invention, which is a set of plural containers serially connected.

Components B as listed in Table 1 were weighed and dissolved by heating at 80° C. This was maintained at 70 to 60° C. and component A was added thereto to give a suspension. A 5 g portion each of the resulting suspension was distributed to each of disposable containers serially connected. The containers were sealed by fusion and cooled to obtain 13 sets of domperidone suspension jellies contained in the disposable containers, for each Example, which were the same as shown by the front view of FIG. 8 except that a set of three containers were serially connected. The serially connected disposable containers used in this Example had an opened spout with a diameter of 4 mm. The completely same containers as these were used in the subsequent Examples.

TABLE 1

| | Blending amount (wt %) | |
|---|---|---|
| Component | Example 1 | Example 2 |
| Component A | | |
| Domperidone | 0.2 | 0.2 |
| Component B | | |
| κ-carrageenan | 0.3 | 0.25 |
| Locust bean gum | 0.3 | 0.25 |
| Sodium polyacrylate | — | 0.01 |
| Sodium citrate | 0.25 | 0.25 |
| Citric acid | 0.05 | 0.05 |
| D-sorbitol | 17.0 | 12.0 |
| Methyl paraben | 0.03 | 0.03 |
| Purified water | 81.87 | 86.96 |

EXAMPLES 3 AND 4

Acyclovir Jelly

Components B as listed in Table 2 were weighed and dissolved by heating at 80° C. This was maintained at 70 to 60° C. and component A was added thereto to give a suspension. A 5 g portion each of the resulting suspension was distributed to each of disposable container serially connected. The containers were sealed by fusion and cooled to obtain 13 sets of 3 disposable containers serially connected, for each Example, which were containing acyclovir suspension jelly.

TABLE 2

| | Blending amount (wt %) | |
|---|---|---|
| Component | Example 3 | Example 4 |
| Component A | | |
| Acyclovir | 8.0 | 8.0 |
| Component B | | |
| κ-carrageenan | 0.4 | 0.5 |
| Locust bean gum | 0.4 | 0.5 |
| Sodium polyacrylate | — | 0.01 |
| Sodium citrate | 0.25 | 0.25 |
| Citric acid | 0.05 | 0.05 |
| D-sorbitol | 17.0 | 12.0 |
| Methyl paraben | 0.03 | 0.1 |
| Purified water | 73.87 | 78.59 |

EXAMPLE 5

Sodium Loxoprofen Jelly

Components B as listed in Table 3 were weighed and dissolved by heating at 80° C. This was maintained at 70 to 60° C. and component A was added thereto and dissolved therein. A 5 g portion each of the resulting solution was distributed to each of disposable container serially connected. The containers were sealed by fusion and cooled to obtain 13 sets of 3 disposable containers serially connected, which were containing sodium loxoprofen jelly.

TABLE 3

| Component | Blending amount (wt %) |
|---|---|
| Component A | |
| Sodium loxoprofen | 1.36 |
| Component B | |
| κ-carrageenan | 0.25 |
| Locust bean gum | 0.25 |
| Sodium polyacrylate | 0.01 |
| Sodium citrate | 0.25 |
| Citric acid | 0.05 |
| D-sorbitol | 12.0 |
| Methyl paraben | 0.1 |
| Purified water | 85.73 |

EXAMPLE 6

Famotidine Jelly

Components B as listed in Table 4 were weighed and dissolved by heating at 80° C. This was maintained at 70 to 60° C. and component A was added thereto and dissolved therein. A 5 g portion each of the resulting solution was distributed to each of disposable container serially connected. The containers were sealed by fusion and cooled to obtain 13 sets of 3 disposable containers serially connected, which were containing famotidine jelly.

TABLE 4

| Component | Blending amount (wt %) |
|---|---|
| Component A | |
| Famotidine | 0.40 |
| Component B | |
| κ-carrageenan | 0.25 |
| Locust bean gum | 0.25 |
| Sodium polyacrylate | 0.01 |
| Sodium ditrate | 0.1 |
| Citric acid | 0.5 |
| D-sorbitol | 12.0 |
| Methyl paraben | 0.1 |
| Purified water | 86.39 |

EXAMPLE 7

Terfenadine Jelly

Components B as listed in Table 5 were weighed and dissolved by heating at 80° C. This was maintained at 70 to 60° C. and component A was added thereto and dissolved therein. A 5 g portion each of the resulting solution was distributed to each of disposable container serially connected. The containers were sealed by fusion and cooled to obtain 13 sets of 3 disposable containers serially connected, which were containing terfenadine jelly.

TABLE 5

| Component | Blending amount (wt %) |
|---|---|
| Component A | |
| Terfenadine | 1.20 |
| Component B | |
| κ-carrageenan | 0.35 |
| Locust bean gum | 0.35 |
| Sodium polyacrylate | 0.01 |
| Sodium citrate | 0.1 |
| Citric acid | 0.5 |
| D-sorbitol | 12.0 |
| Methyl paraben | 0.1 |
| Purified water | 85.39 |

REFERENCE EXAMPLE

Sweet Jelly

Components B as listed in Table 6 were weighed and dissolved by heating at 80° C. This was maintained at 70 to 60° C. and component A was added thereto and dissolved therein. The resulting solution was distributed to 30 containers for sweet jelly. The containers were sealed and cooled to obtain sweet jellies.

TABLE 6

| Component | Blending amount (wt %) |
|---|---|
| Component A | |
| Orange juice | 10.0 |
| Component B | |
| κ-carrageenan | 0.4 |
| Locust bean gum | 0.4 |
| Sodium polyacrylate | 0.01 |

TABLE 6-continued

| Component | Blending amount (wt %) |
|---|---|
| Sodium citrate | 0.25 |
| Citric acid | 0.05 |
| Purified sugar | 8.0 |
| Methyl paraben | 0.03 |
| Colorant | 0.01 |
| Purified water | 80.85 |

Evaluation of the jellied medical composition for oral administration of the present invention The jellied medical compositions for oral administration obtained in each Example as described above were subjected to a test for easiness to swallow, a test for taking out of the container, and a stability test.

(1) Test for easiness to swallow

In order to evaluate each jellied composition prepared in Example 2 and Examples 4 through 7 for their easiness to swallow by human subjects, jellied compositions contained in the serially connected disposable containers were prepared in the same manner as described above to have the same compositions in the respective Examples except for using purified water in place of component A, which is an effective medical component in the compositions of the respective Examples, Further, the same jellied compositions were prepared, which were not contained in the serially connected disposable containers but were allowed to gel in the containers usually used for jelly for food. The jellied compositions for comparison with those of Example 2 and Examples 4 through 7, which were allowed to gel in the containers usually used for jelly for food, were designated as sample Nos. 1 to 5, while the jellied compositions contained in serially connected disposable containers for comparison with those of Example 2 and Examples 4 through 7 were designated as sample Nos. 6 to 10.

The thus-obtained jellied composition sample Nos. 1 to 10 were subjected to a test for easiness to swallow by 12 panelists (the respective panelists were designated as A through L).

Each panelist took a spoonful of each jellied composition of sample Nos. 1 to 5 using a spoon. With respect to the jellied compositions contained in the disposable containers of sample Nos. 6 to 10, each panelist opened one container for each jellied composition, put the jellied composition directly into the mouth from the spout of the container, and then, swallowed it. Subsequently, the sensory evaluation for easiness to swallow (texture felt at the throat) was performed based on the following criteria. For comparison, using commercially available food for swallowing aids as highly viscous liquid compositions, the sensory evaluation for easiness to swallow was performed by the same 12 panelists as above. The results are shown in Table 7.

Criteria for evaluation

⊙: easy to swallow

○: slightly easy to swallow

Δ: slightly difficult to swallow

X: difficult to swallow

TABLE 7

| Sample No\Panelist | A | B | C | D | E | F | G | H | I | J | K | L |
|---|---|---|---|---|---|---|---|---|---|---|---|---|
| Sample 1 | ○ | ○ | ○ | ○ | ○ | ○ | ○ | ○ | ○ | ○ | ○ | ○ |
| Sample 2 | Δ | ○ | ○ | Δ | ○ | ○ | Δ | ○ | ○ | ○ | ○ | Δ |
| Sample 3 | Δ | ○ | ○ | ○ | ○ | ○ | ○ | ○ | ○ | ○ | ○ | ○ |
| Sample 4 | ○ | ○ | ○ | ○ | ○ | ○ | ○ | ○ | ○ | ○ | ○ | ○ |
| Sample 5 | ○ | ○ | ○ | ○ | ○ | ○ | ○ | ○ | ○ | ○ | ○ | ○ |
| Sample 6 | ⊙ | ⊙ | ⊙ | ⊙ | ⊙ | ⊙ | ⊙ | ⊙ | ⊙ | ⊙ | ⊙ | ⊙ |
| Sample 7 | ○ | ⊙ | ⊙ | ○ | ○ | ⊙ | ○ | ⊙ | ⊙ | ⊙ | ○ | ○ |
| Sample 8 | ⊙ | ⊙ | ⊙ | ⊙ | ⊙ | ⊙ | ⊙ | ⊙ | ⊙ | ⊙ | ⊙ | ⊙ |
| Sample 9 | ⊙ | ⊙ | ⊙ | ⊙ | ⊙ | ⊙ | ⊙ | ⊙ | ⊙ | ⊙ | ⊙ | ⊙ |
| Sample 10 | ⊙ | ⊙ | ⊙ | ⊙ | ⊙ | ⊙ | ⊙ | ⊙ | ⊙ | ⊙ | ⊙ | ⊙ |
| Food for swallowing aids | x | x | Δ | x | Δ | x | x | x | Δ | x | x | x |

The same results as above were obtained when the same tests were carried out for the jellied compositions of Example 1 and Example 3.

From these results, it can be understood that the jellied medical compositions for oral administration of the present invention have remarkably improved easiness to take as compared with the conventional highly viscous liquid compositions. Particularly, the jellied medical compositions for oral administration in the disposable container of the present invention are crushed into appropriate pieces when pushed out through the spout of the container and are to be taken with solidity suitable for swallowing and with good texture, which reveals that the compositions have great easiness to take.

(2) Test for taking out

The test for taking out of the container was carried out using 3 sets of 3 containers serially connected, namely 9 containers in total, of each jellied medical composition for oral administration in the disposable container obtained in Examples 1 to 7. As a result, all of the jellied compositions were taken out without adhering to the containers.

(3) Stability test of the jellied medical compositions for oral administration

Ten sets of 3 containers serially connected, namely 30 containers in total, of each jellied medical composition for oral administration in the disposable container obtained in Example 2 and Examples 4 to 7 and 30 sweet jellies in the containers obtained in Reference Example were allowed to stand for 3 months at 40° C. and 75% RH. Thereafter, the jellied compositions were taken out of all of the containers and observed by naked eyes as to whether syneresis occurred or not.

As a result, there was found little syneresis among all the jellied compositions of the above Examples and sweet jellies of Reference Example prepared by using, as a base, carrageenan, locust bean gum, and sodium polyacrylate.

From this result, it can be understood that the jellied medical compositions for oral administration of the present invention containing a base having a specific composition do not cause syneresis even in the medical level test and retain preservation stability.

INDUSTRIAL APPLICABILITY

The jellied medical compositions for oral administration of the present invention can be easily taken even by patients of advanced age or patients with dysphagia. Further, the jellied medical compositions for oral administration of the present invention containing a base having a specific composition do not easily cause syneresis and retain preservation stability at the medical level in terms of maintenance of appearance and pH of the composition and maintenance of dispersibility and the contents of the effective components in the composition. Furthermore, a predetermined dose of the jellied composition can be taken with solidity suitable for swallowing and with good texture when using the jellied medical compositions for oral administration in the disposable container of the present invention. Thus, safety and easiness to take the medical composition for oral administration are secured for, particularly, patients of advanced age or patients with dysphagia, and improved compliance can be expected.

What is claimed is:

1. A jellied medical composition for oral administration, which comprises, as a base, carrageenan and locust bean gum.

2. The jellied medical composition for oral administration according to claim 1, wherein said carrageenan is contained in an amount of 0.01 to 1.0 wt % based on the total weight of the composition.

3. The jellied medical composition for oral administration according to claim 1, wherein said locust bean gum is contained in an amount of 0.01 to 1.0 wt % based on the total weight of the composition.

4. The jellied medical composition for oral administration according to claim 1, which further comprises, as the base, polyacrylic acid or a partly neutralized product or salt thereof.

5. The jellied medical composition for oral administration according to claim 4, wherein said salt of polyacrylic acid is sodium polyacrylate.

6. The jellied medical composition for oral administration according to claim 4, wherein said polyacrylic acid or partly neutralized product or salt thereof is contained in an amount of 0.005 to 0.05 wt % based on the total weight of the composition.

7. The jellied medical composition for oral administration according to claim 1, which is contained in a disposable container made of a synthetic resin and composed of a shell being deformable under forcing and capable of containing the jellied medical composition for oral administration therein, a ring neck with a small diameter connected to the shell, and a handle serving as the closed end of the neck and connected to the neck in a breakable manner, wherein the neck is opened to provide a spout for pouring the jellied medical composition for oral administration when the handle is broken away from the neck.

8. The jellied medical composition for oral administration in the disposable container according to claim 7, wherein a content of the jellied medical composition for oral administration in the disposable container is equal to a dose of the composition.

9. The jellied medical composition for oral administration in the disposable container according to claim 7, wherein a diameter of the spout formed when the handle is broken away from the neck ranges from 1 to 15 mm.

* * * * *